United States Patent
Matsumura et al.

(10) Patent No.: US 11,602,146 B2
(45) Date of Patent: Mar. 14, 2023

(54) CONNECTOR AND FLUID SUPPLY SYSTEM

(71) Applicants: National University Corporation Kitami Institute of Technology, Hokkaido (JP); National University Corporation Asahikawa Medical University, Hokkaido (JP)

(72) Inventors: Masanori Matsumura, Hokkaido (JP); Naoto Matsuno, Asahikawa (JP); Jun-Ichi Shibano, Hokkaido (JP); Yutaka Yoshida, Hokkaido (JP); Michihiro Sato, Hokkaido (JP); Hiroyuki Furukawa, Hokkaido (JP)

(73) Assignees: National University Corporation Kitami Institute of Technology, Hokkaido (JP); National University Corporation Asahikawa Medical University, Hokkaido (JP)

( * ) Notice: Subject to any disclaimer, the term of this patent is extended or adjusted under 35 U.S.C. 154(b) by 641 days.

(21) Appl. No.: 16/499,004

(22) PCT Filed: Mar. 15, 2018

(86) PCT No.: PCT/JP2018/010221
§ 371 (c)(1),
(2) Date: Mar. 25, 2020

(87) PCT Pub. No.: WO2018/180544
PCT Pub. Date: Oct. 4, 2018

(65) Prior Publication Data
US 2020/0383319 A1    Dec. 10, 2020

(30) Foreign Application Priority Data
Mar. 30, 2017  (JP) .............................. JP2017-067202

(51) Int. Cl.
*A01N 1/02* (2006.01)
*A61M 25/10* (2013.01)

(52) U.S. Cl.
CPC ..... *A01N 1/0247* (2013.01); *A61M 25/10181* (2013.11); *A61M 2025/107* (2013.01);
(Continued)

(58) Field of Classification Search
CPC ............ A01N 1/0247; A61M 39/0247; A61M 2039/0297; A61M 2039/0258;
(Continued)

(56) References Cited

U.S. PATENT DOCUMENTS

| 4,473,637 A | 9/1984 | Guibert |
| 6,358,266 B1 * | 3/2002 | Bonutti ................. A61M 29/02 604/103.08 |
| 8,460,168 B2 * | 6/2013 | Farnan ................... A61M 27/00 600/16 |
| 9,463,268 B2 * | 10/2016 | Spence ............... A61M 1/3653 |

(Continued)

FOREIGN PATENT DOCUMENTS

| CN | 103648411 A | 3/2014 |
| CN | 104619167 A | 5/2015 |

(Continued)

*Primary Examiner* — Nathan R Price
*Assistant Examiner* — Melissa A Snyder
(74) *Attorney, Agent, or Firm* — Gordon Rees Scully Mansukhani, LLP

(57) ABSTRACT

A connector (1) includes: a tube (10) configured to be arranged in an interior of a vascular channel; a tubular body (30) having an inner wall surface configured to, together with an outer wall surface of the tube (10), sandwich the vascular channel when the tube (10) is arranged in the interior of the vascular channel; and a balloon (20), configured to be arranged on the outer wall surface of the tube (10) or the inner wall surface of the tubular body (30), and radially expand for performing sealing (i) between the soft
(Continued)

tubular member and the inner wall surface of the tubular body (30) and (ii) between the soft tubular member and the outer wall surface of the tube (10). A fluid supply system (100) may include the connector (1), and a perfusion solution supply device (120) connected to the connector (1) and configured to supply a perfusion solution into the interior of the vascular channel.

16 Claims, 26 Drawing Sheets

(52) U.S. Cl.
CPC ............... *A61M 2025/1088* (2013.01); *A61M 2205/3331* (2013.01)

(58) Field of Classification Search
CPC .... A61M 2039/0261; A61M 60/30–39; A61M 1/3613; A61M 25/1081; A61M 2025/107; A61B 2017/1107
See application file for complete search history.

(56) References Cited

U.S. PATENT DOCUMENTS

| | | | |
|---|---|---|---|
| 10,028,741 B2* | 7/2018 | Jimenez | ............. A61B 17/0057 |
| 2003/0158563 A1* | 8/2003 | McClellan | ....... A61B 17/12013 |
| | | | 606/151 |
| 2009/0123993 A1 | 5/2009 | Banes et al. | |
| 2012/0277687 A1 | 11/2012 | Kravitz et al. | |
| 2014/0329220 A1 | 11/2014 | Steinman et al. | |
| 2017/0064943 A1 | 3/2017 | Ritchie et al. | |
| 2017/0156573 A1 | 6/2017 | Takemoto | |

FOREIGN PATENT DOCUMENTS

| | | |
|---|---|---|
| CN | 106793927 A | 5/2017 |
| EP | 3263010 A1 | 1/2018 |
| JP | 2014-518680 A | 8/2014 |
| JP | 2015-524393 A | 8/2015 |
| JP | WO2016/136514 A1 | 9/2016 |
| WO | 2012/148685 A1 | 11/2012 |
| WO | 2014/011539 A2 | 1/2014 |
| WO | 2017/044465 A1 | 3/2017 |

* cited by examiner

FIRST CROSS-SECTIONAL SHAPE | SECOND CROSS-SECTIONAL SHAPE | THIRD CROSS-SECTIONAL SHAPE | FOURTH CROSS-SECTIONAL SHAPE | FIFTH CROSS-SECTIONAL SHAPE

CONNECTOR AND FLUID SUPPLY SYSTEM

TECHNICAL FIELD

The present disclosure relates to a connector and a fluid supply system, and particularly relates to a connector and a fluid supply system that are connectable to a vascular channel of an organ.

BACKGROUND ART

In order to preserve an organ harvested from a donor for transplant, technology is known for connecting to a vascular channel of the organ a perfusion device for supply of a perfusion solution, that is, a pharmaceutical liquid such as physiological saline solution, to the vascular channel. For example, Patent Literature 1 mentions a connector that is equipped with a top portion and a bottom portion for sandwiching and fixing the vascular channel of the organ, and a compression strap for pushing together the top portion and the bottom portion. A tube for supplying the perfusion solution is connected to the top portion, and the connector of Patent Literature 1 supplies the perfusion solution to the vascular channel sandwiched by the top portion and the bottom portion.

CITATION LIST

Patent Literature

Patent Literature 1: Unexamined Japanese Patent Application Kokai Publication (Translation of PCT Application) No. 2005-536321

SUMMARY OF INVENTION

Technical Problem

To prevent deterioration of the harvested organ from the donor, the perfusion device is to be quickly connected to the vascular channel of the organ and then the organ is to be quickly perfused. Further, in order to make the organ transplant easier for the physician, damage to the vascular channel tissue is to be avoided as much as possible, and thus an effective length of the vascular channel is to be secured. However, the connector of Patent Literature 1 sandwiches the vascular channel by the top portion and the bottom portion, and further fixes by compression using the compression strap, and thus problems arise in that time is expended in attachment to and detachment from the vascular channel, and the vascular channel tissue is easily damaged. These problems are not limited to the case of connection of a connector to a vascular channel of the organ harvested from a donor, but rather exist is various technical fields relating to the connection together of a soft tubular member and a connector.

In consideration of the aforementioned circumstances, an objective of the present disclosure is to provide a connector and a fluid supply system capable of easy attachment to and detachment from a soft tubular member in a short period without damaging the soft tubular member.

Solution to Problem

In order to attain the aforementioned objective, a connector according to a first aspect of the present disclosure includes:

a tube configured to be arranged in an interior of a soft tubular member;

a tubular body having an inner wall surface configured to, together with an outer wall surface of the tube, sandwich the soft tubular member when the tube is arranged in the interior of the soft tubular member; and a balloon, configured to be arranged on the outer wall surface of the tube or the inner wall surface of the tubular body, and radially expand for performing sealing (i) between the soft tubular member and the inner wall surface of the tubular body and (ii) between the soft tubular member and the outer wall surface of the tube.

The balloon may be disposed so as to surround the outer wall surface of the tube or the inner wall surface of the tubular body in the circumferential direction, and when expanded, may perform sealing between the soft tubular member and the inner wall surface or the outer wall surface.

A concavity may be formed in the inner wall surface of the tubular body at a part contacting the expanded balloon, or a concavity may be formed in the outer wall surface of the tube at a part contacting the expanded balloon.

A groove, a protuberance, or an unevenness for suppressing slippage of the soft tubular member may be formed in the inner wall surface of the tubular body or the outer wall surface of the tube.

The balloon may be arranged on the outer wall surface of the tube and is configured to radially expand toward the inner wall surface of the tubular body, and the tubular body may include a plurality of members that are mutually separable, and are integrated into a single body by assembly.

The connector may further include coupling means for coupling together the tube, and the tubular body such that the tubular body is movable relative to the tube.

The coupling means may be formed so as to expand and contract with elastic deformability in a longitudinal axis direction of the tube.

The coupling means may include (i) a tubular member formed from an elastic material and (ii) a plurality of slits formed in the longitudinal axis direction of the tubular member.

The coupling means may be a tubular cover that is closely contactable with and fixable to the tube and the tubular body, and may sealably enclose a fluid in an interior of the tubular cover.

In order to achieve the aforementioned objective, a fluid supply system according to a second aspect of the present disclosure includes:

the connector; and a fluid supply device configured to supply a fluid into the interior of the soft tubular member and connectable to the connector.

The fluid supply system may include:

fluid supply means for supplying the fluid into the balloon;

pressure measurement means for measuring a fluid pressure within the balloon; and control means for, based on a result of the measurement of the pressure measurement means, controlling the fluid supply means to maintain the fluid pressure within the balloon at a set value.

Advantageous Effects of Invention

According to the present disclosure, a connector and a fluid supply system can be provided that are capable of easy attachment to and detachment from the soft tubular member in a short period without damaging the soft tubular member.

DESCRIPTION OF EMBODIMENTS

Embodiments of the connector of the present disclosure are described below in detail with reference to drawings. In each of the drawings, components that are the same or equivalent are assigned the same reference sign. In each of the embodiments, orthogonal coordinates are used in which an X axis refers to a direction of extension of a tube, a Y axis refers to a direction that is perpendicular to the X axis and is on a horizontal plane that includes the tube, and a Z axis refers to direction (vertical direction) perpendicular to the X and Y axes.

In each of the embodiments, the term "soft tubular member" is taken to mean a tube that is elastically deformable so as to closely contact another tube. The meaning of the term "soft tubular member", in addition to meaning tubular living tissue such as a blood vessel, a vascular channel, a lymph vessel, a ureter, a urethra, an intestinal canal, a bronchial tube, or the like, is taken to include a tube made of a resin material, a metal material, rubber, an elastomer, or the like.

Embodiment 1

A connector 1 and a fluid supply system 100 according to Embodiment 1 are described with reference to FIGS. 1A to 4. Although in the embodiment below an example is described in which the connector 1 is connected to a vascular channel of a organ and a perfusion solution is supplied to the vascular channel, the target of connection of the connector 1 is not limited to the vascular channel, and the supplied fluid is not limited to the perfusion solution.

Figure 1A:
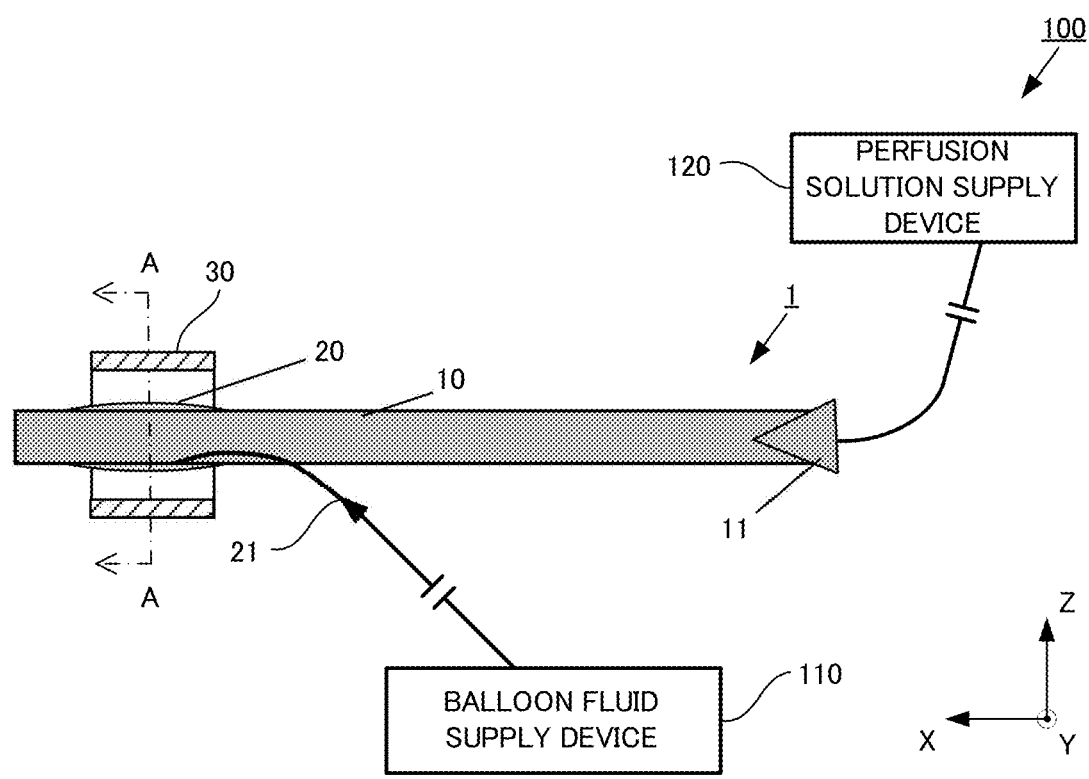
FIG. 1A is a cross-sectional view illustrating a connector according to Embodiment 1 of the present disclosure.
Figure 1B:
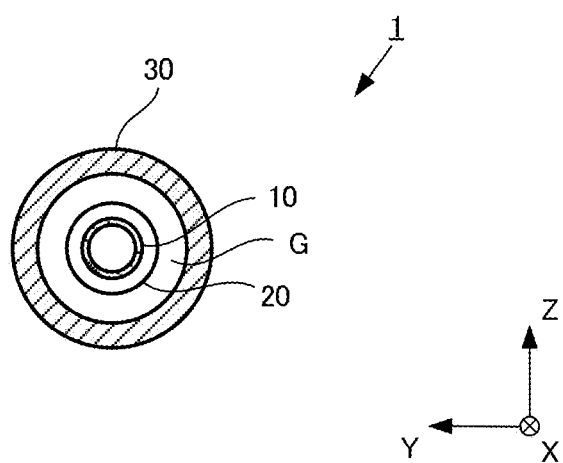
FIG. 1B is a cross-sectional view taken along line A-A of the connector illustrated in FIG. 1A.

FIG. 1A is a side view illustrating the connector 1 according to Embodiment 1 of the present disclosure, and FIG. 1B is a cross-sectional view taken along line A-A of the connector 1 illustrated in FIG. 1A. To facilitate understanding, FIG. 1A illustrates a balloon 20 and a tubular body 30 in cross section. As illustrated in FIGS. 1A and 1B, the connector 1 is equipped with a tube 10, the balloon 20 fixed to an outer wall portion of the tube 10 and is arranged at a distal side of the tube 10, and the tubular body 30 that is a separate member from the tube 10 and is arrangeable so as to cover a circumference of the balloon 20. A gap G in which the vascular channel is arrangeable is formed between the outer wall portion of the tube 10 and the interior wall portion of the tubular body 30.

The tube 10 is a tubular member that is capable of supplying the perfusion solution from a base part toward a distal part. In an interior of the tube 10, a tubular path is formed for enabling passage of the perfusion solution, and an opening is formed at each of the distal part and the base part of the tube 10. The tube 10 may be a flexible tube capable of bending deformation or may be a rigid tube that tends not to undergo bending deformation.

At the base part of the tube 10, a connection member 11 is provided that is connected to a perfusion solution supply device 120 for supplying the perfusion solution. When the perfusion solution supply device 120 is connected to the connection member 11, the perfusion solution supplied from the perfusion solution supply device 120 is supplied to the tubular path of the tube 10 through the connection member 11 and is discharged to the exterior from the opening in the distal part of the tube 10.

The balloon 20 is a membrane-like member that is radially expandable due to the supply of a fluid into the interior. The balloon 20 is a cylindrically shaped membrane-like member that closely contacts, and is fixed to, the outer wall portion of the tube 10 at the distal side and the base side. Thus a sealed space is formed at the interior between the interior wall portion of the balloon 20 and the outer wall portion of the tube 10. The balloon 20 is formed from an elastic material such as rubber, an elastomer, or the like that has the property of stretching due to pressure from a fluid.

A balloon injection tube 21 is connected to the balloon 20 and configured to supply a fluid into the balloon 20. Upon supply of the fluid into the interior of the balloon 20 from the balloon injection tube 21, the balloon 20 expands in the radial direction and assumes an approximate spindle shape. Moreover, upon suction of the fluid via the balloon injection tube 21 from the interior of the balloon 20, the balloon 20 shrinks in the radial direction.

Further, the tube 10 and the balloon 20 may be a widely-known balloon catheter, for example. The balloon catheter is equipped internally with a catheter main body having a tubular path, and an expandable balloon provided at a distal part of the catheter main body.

The tubular body 30 is a tubular member capable of covering from the exterior side a perimeter of the balloon 20. The tubular body 30 has greater rigidity than the balloon 20 and is configured so as not to deform even when the interior wall portion is compressed by the expanded balloon 20. The tubular body 30 is formed by a material such as a metal material, a resin material, rubber, an elastomer, cloth, and the like, for example.

The interior wall portion of the tubular body 30 may be surface-processed such that, upon contacting the vascular channel, frictional force is generated between the interior wall portion and the vascular channel. For example, the inner wall surface of the tubular body 30 may be provided with grooves, protuberances, irregularities, or the like.

A protuberance, a concavity, or an unevenness or the like may be arranged on the outer wall portion of the tubular body 30 for easy grasping of the tubular body 30 by the user. For example, the tubular body 30 may be provided with a pair of protuberances, concavities, unevenness, or the like on both sides of a surface part of the tubular body 30 to enable grasping by the thumb and index finger of the user.

Figure 2A:
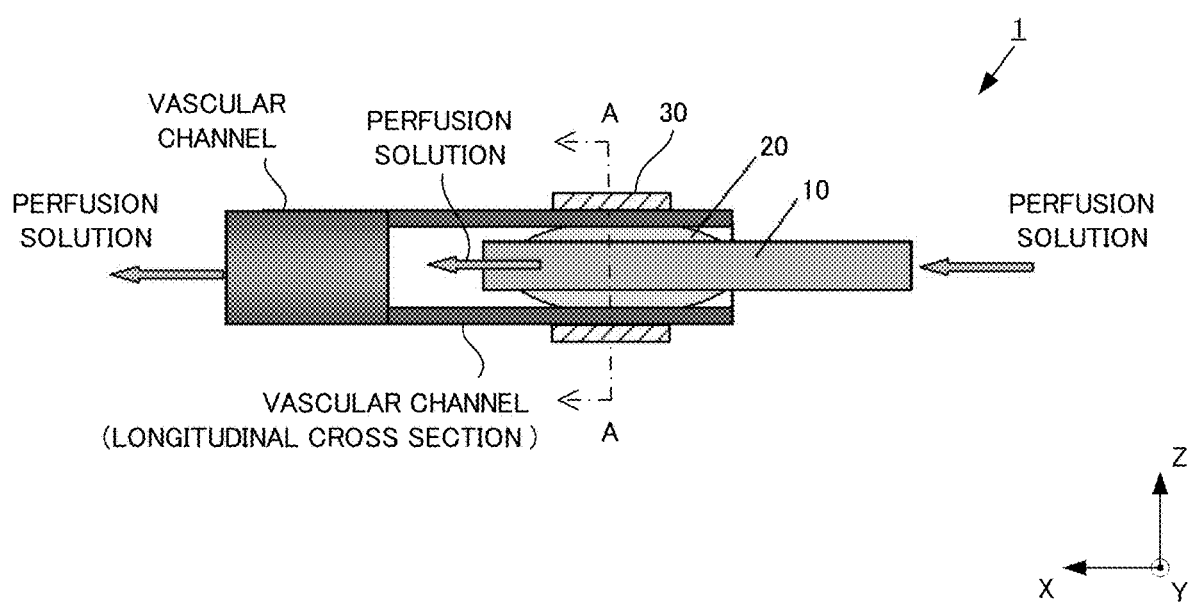
FIG. 2A is a side cross-sectional view illustrating connection of the connector of FIGS. 1A and 1B to a vascular channel.
Figure 2B:
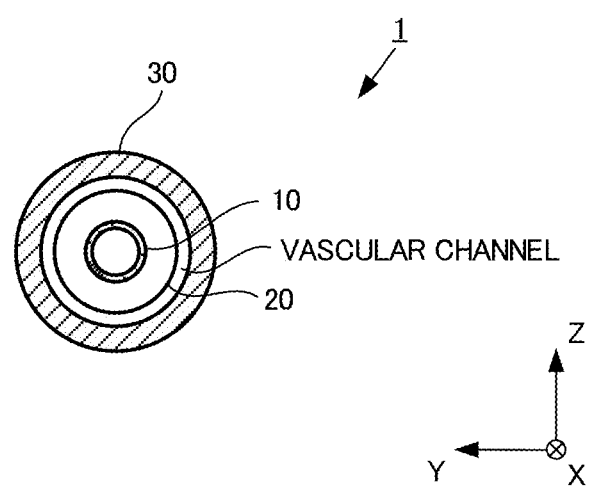
FIG. 2B is a cross-sectional view taken along line A-A of the connector illustrated in FIG. 2A.

Next, a mechanism for connection of the connector 1 to the vascular channel is described with reference to FIGS. 2A and 2B. FIG. 2A is a cross-sectional view illustrating attachment of the connector 1 to the vascular channel, and FIG. 2B is a cross-sectional view taken at line A-A of the connector 1 illustrated in FIG. 2A. To facilitate understanding, part of the vascular channel, and the balloon 20 and the tubular body 30, are illustrated in cross section in FIG. 2A.

During attachment of the connector 1 to the vascular channel, the balloon 20 is inserted into the interior of the vascular channel, and the tubular body 30 is arranged so that the balloon 20 is covered from the outside by the vascular channel. Upon supply of fluid to the balloon 20 in the state to cause the balloon 20 to expand in the radial direction, the vascular channel is pushed and widened radially by the balloon 20, and is pressed against the interior wall portion of the tubular body 30.

At this time, the vascular channel is sandwiched between the outer wall portion of the balloon 20 and the interior wall portion of the tubular body 30, thereby sealing the vascular channel by the surface of the outer wall portion of the balloon 20 and the surface of the interior wall portion of the tubular body 30. Thus when the perfusion solution is supplied from the tube 10 to the vascular channel, leakage of the perfusion solution from the connection member connecting the vascular channel and the connector 1 does not occur. Moreover, frictional force is generated by surface contact between the interior wall portion of the vascular channel and the outer wall portion of the balloon 20 and between the outer wall portion of the vascular channel and the interior wall portion of the tubular body 30, and thus the connector 1 does not fall out of the vascular channel.

Further, the supplying of the fluid to the balloon 20 via the connector 1 enables connection of the vascular channel to the connector 1, and discharge of the fluid from the balloon 20 enables release of the vascular channel from the connector 1. Thus the user can easily in a short period attach the connector 1 to the vascular channel and detach the connector 1 from the vascular channel. The vascular channel is sandwiched between the surface of the outer wall portion of the balloon 20 and the surface of the interior wall portion of the tubular body 30, and the connector 1 does not apply high pressure locally to the vascular channel. Such operation can prevent damage to the vascular channel tissue caused by connection of the connector 1 to the vascular channel.

Again with reference to FIG. 1, the fluid supply system 100 equipped with the connector 1 is described. The fluid supply system 100 is equipped with the connector 1 that is connectable to the vascular channel, a balloon fluid supply device 110 that supplies the fluid to the balloon 20 of the connector 1 to control expansion of the balloon 20, and a perfusion solution supply device 120 that supplies the perfusion solution to the tubular path of the connector 1.

The perfusion solution supply device 120 is a device capable of supplying the perfusion solution to the tubular path of the connector 1 at a flow rate, timing, or the like predetermined by the user. The perfusion solution supply device 120 is equipped with a command receiver and a controller. The command receiver receives from the user commands such as a command to start perfusion, a time to end perfusion, a setting value of the flow rate of the perfusion solution, or the like. On the basis of the command received by the command receiver, the controller controls perfusion from the perfusion solution supply device 120 to the vascular channel.

More specifically, the controller firstly acquires from a flow rate sensor arranged in the tubular path measurement data relating to the flow rate of the perfusion solution. Then the controller controls operation of a pump supplying the perfusion solution to the vascular channel such that a difference between the measurement value of the flow rate of the perfusion solution and a setting value becomes less than a predetermined threshold. The controller also controls operation of the pump to continue the perfusion into the vascular channel at a fixed flow rate until the present time reaches the completion time of perfusion.

Figure 3:
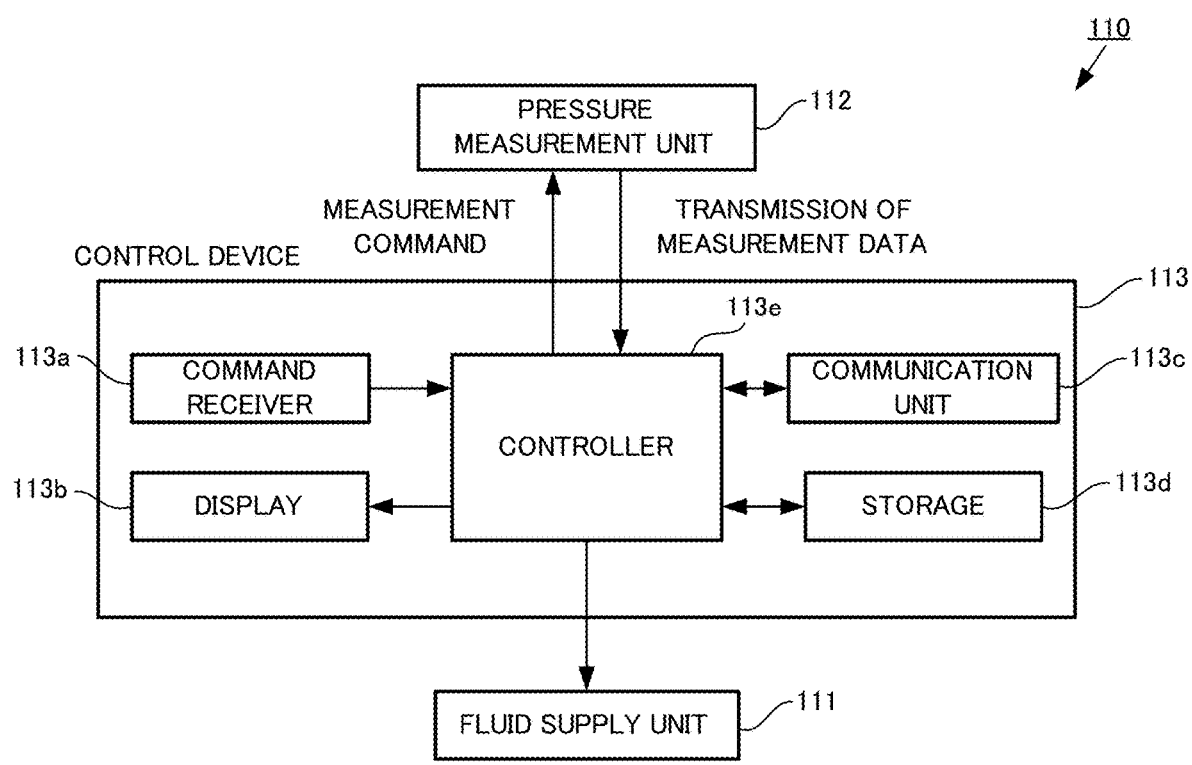
FIG. 3 is a block diagram of a balloon fluid supply device according to Embodiment 1 of the present disclosure.

FIG. 3 is a block diagram illustrating configuration of the balloon fluid supply device 110. As illustrated in FIG. 3, the balloon fluid supply device 110 is equipped with a fluid supply unit 111, a pressure measurement unit 112, and a control device 113.

The fluid supply unit 111 is an example of a fluid supply means for supplying the fluid to the interior of the balloon 20 in order to expand the balloon 20. The fluid supply unit 111 is configured from components such as a pump, for example, and is connected to the tube 10.

The pressure measurement unit 112 is an example of a pressure measurement means for measurement of pressure of the fluid supplied to the interior of the balloon 20. The pressure measurement unit 112 is equipped with a pressure sensor, for example, and is arranged at a position such as a tubular path for supply of the fluid arranged in the interior of the balloon fluid supply device 110. Examples of locations at which the pressure measurement unit 112 may be arranged include the interior of the balloon 20, the balloon injection tube 21, or the like.

The control device 113 is an example of a control means for control of operation of various components of the fluid supply system 100 on the basis of the measurement data of the fluid pressure measured by the pressure measurement unit 112. The control device 113 is equipped with a command receiver 113a, a display 113b, a communication unit 113c, a storage 113d, and a controller 113e. The command receiver 113a, the display 113b, the communication unit 113c, and the storage 113d are mutually-communicatively connected to the controller 113e via a wired or wireless communication line.

The command receiver 113a receives an command from the user and supplies to the controller 113e an operation signal corresponding to the received operation. The command receiver 113a includes, for example, buttons, a keyboard, a mouse, a joystick, or the like. The command receiver 113a may be a device such as a connector that is connectable to a device such as an external command device.

The display 113b displays graphic content such as various types of images based on data such as various types of image data supplied from the controller 113e. The display 113b is equipped with an liquid crystal panel or an organo-electro-luminescence (EL) panel. The display 113b may be a device such as an external display device that is connectable via a connector with which the control device 113 is provided.

The command receiver 113a and the display 113b may be mutually integrated by use of a touch panel. In addition to displaying an operation screen for receiving a prescribed operation, the touch panel supplies to the controller 113e an operation signal corresponding to a position of a touch operation by the user touching the operation screen.

The communication unit 113c is an interface that is capable of connection to a communication network such as the Internet. The communication unit 113c communicates via the communication network with an external terminal, a server, a memory, or the like. For example, the communication unit 113c may transmit to the external terminal the measurement value of the fluid pressure within the balloon 20 and may receive from the external terminal a setting value of the fluid pressure within the balloon 20.

Figure 4:
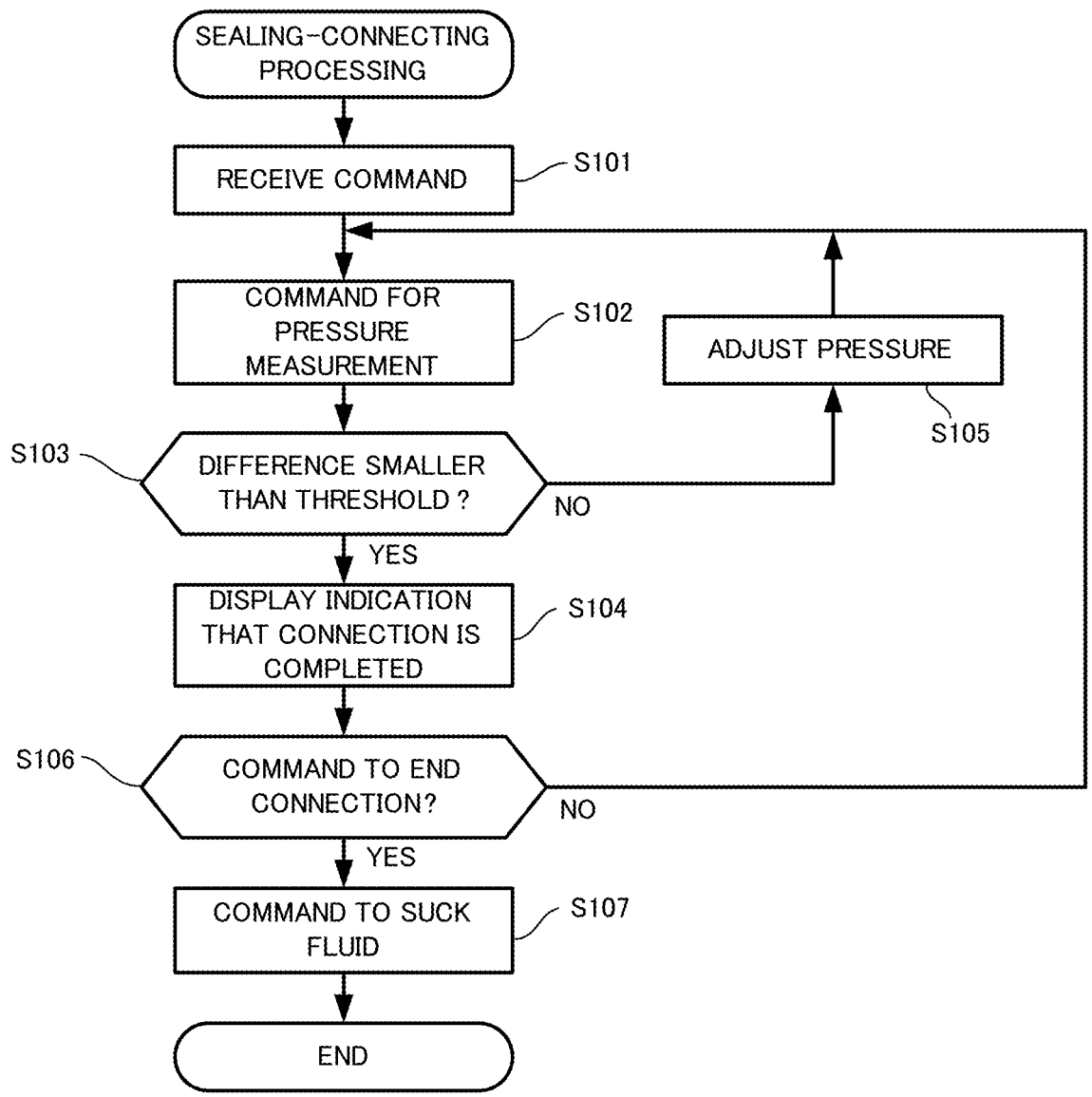
FIG. 4 is a flowchart of sealing-connecting processing according to Embodiment 1 of the present disclosure.

The storage 113d is equipped with a random access memory (RAM), a read only memory (ROM), a hard disk device, a flash memory, or the like, and stores programs and various types of data for the sealing-connecting processing of FIG. 4 that is executed by the controller 113e. Moreover, the storage 113d functions as working memory for the controller 113e to execute processing.

The controller 113e is equipped with a processor, such as a central processing unit (CPU), and performs control of various components of the control device 113. The controller 113e executes the sealing-connecting processing of FIG. 4 by executing the programs stored in the storage 113d. Specifically, the controller 113e controls operation of the fluid supply unit 111 such that the difference between the measured value of the fluid pressure within the balloon 20 and the setting value of the fluid pressure set by the user becomes as close as possible to zero. More specifically, the controller 113e controls the operation of the fluid supply unit 111 such that the difference between the measurement value of the fluid pressure within the balloon 20 and the setting value of the fluid pressure set by the user becomes less than a threshold. The setting value of the fluid pressure, for example, is set by the user in consideration of the material and size of the balloon 20, the type, size, and degree of damage to the vascular channel, the type and flow rate of the perfusion solution, or the like. The threshold is a set value determined beforehand by the user, and for example, is determined in consideration of information such as the type, size, extent of damage, or the like of the vascular channel.

The control device 113 may be achieved by a dedicated system, or may be achieved by use of a small-sized general-purpose computer. The processing executed by the control device 113, for example, is achieved by a device equipped with the above-described physical configuration executing a program stored in the storage 113d. The present disclosure may be achieved by a program, and the program may be achieved by use of a recording medium that records the program.

The method of use of the connector 1 according to Embodiment 1 is described next. Processing is taken to be previously performed, such as connection of the tube 10 to the perfusion solution supply device 120 via tubing and deaeration.

Firstly, the user, such as a physician, removes the organ from within the body of the donor. Next, the user inserts the tube 10 so as to entirely hide the balloon 20 within the vascular channel of the removed organ. At this time, the tubular body 30 is taken to be disposed at the base side of the tube 10. Next, the user grasps the tubular body 30 by using the thumb and index finger, and thus moves the tubular body 30 to the distal side of the tube 10 so that the balloon 20 covered by the vascular channel is further covered from the exterior.

Next, the user causes the fluid supply system 100 to execute the sealing-connecting processing of FIG. 4, and causes expansion of the balloon 20 at a predetermined fluid pressure. Due to execution of the sealing-connecting processing of FIG. 4, the connector 1 is connected, in a state in which the vascular channel is entirely sealed, so as to not not fall out of the vascular channel. Next, the user operates the perfusion solution supply device 120 to start the supply of the perfusion solution to the vascular channel. Due to the ability to continuously supply the perfusion solution to the organ, the organ can be stored until transplant without deterioration. The organ may be transported to another facility while continuing the perfusion of the organ.

Prior to the start of the transplant of the organ, the user operates the perfusion solution supply device 120 to stop the supply of the perfusion solution to the vascular channel. Next, the user gives a command to the fluid supply system 100 to stop the sealing-connecting processing of FIG. 4. Upon giving of the command, the fluid supply system 100 causes the balloon 20 to shrink in the radial direction, and thus while holding the vascular channel, and with completion of the shrinking, the user pulls the tube 10 out of the vascular channel. After removal of the connector 1 from the vascular channel, the user places the organ in a body cavity of a patient, and starts the transplant of the organ. The series of processing for perfusion of the vascular channel of the organ using the connector 1 ends due to the aforementioned steps.

The sealing-connecting processing executed by the fluid supply system 100 is described next with reference to the flowchart of FIG. 4. The sealing-connecting processing is processing for connection of the connector 1 to the vascular channel in a sealed state.

Firstly, the user uses the command receiver 113a to set the pressure to be applied to the balloon 20, and gives a command to start the expansion of the balloon 20. The command receiver 113a receives the command from the user to start the expansion of the balloon 20 (step S101). The command receiver 113a supplies to the storage 113d the setting value, set by the user, for the fluid pressure within the balloon 20.

After passage of a prescribed period after the processing of step S101, such as a period within a range of 10 seconds to 10 minutes set by the user, the controller 113e commands that the pressure measurement unit 112 measures the fluid pressure within the balloon 20 (step S102). The pressure measurement unit 112 measures the fluid pressure within the balloon 20 and transmits the measurement data to the controller 113e.

Next, the controller 113e determines whether the difference between the measurement value of the fluid pressure within the balloon 20 and the setting value of the fluid pressure set by the user is smaller than the threshold (step S103). When the difference is smaller than the threshold (YES in step S103), the display 113b displays indication that the vascular channel and the connector 1 are connected appropriately and that the connection is completed (step S104).

When the difference is equal to the threshold or is larger than the threshold (NO in step S103), the controller 113e controls operation of the fluid supply unit 111 to adjust the fluid pressure within the balloon 20 (step S105), and processing returns to step S102. Then the processing of steps S102, S103, and S105 is repeated until the difference becomes less than the threshold.

After execution of the processing of step S104, the command receiver 113a determines whether a command is received from the user commanding the ending of the connection of the connector 1 (step S106). Upon receiving from the user the command to end the connection of the connector 1 (YES in step S106), the controller 113e commands the fluid supply unit 111 to suck the fluid from the balloon 20 (step S107), and the processing ends. When the user instruction to end the connection of the connector 1 is not received (NO in step S106), after passage of the prescribed period, processing returns to step S102, and the processing of steps S102 to S106 is repeated. The sealing-connecting processing is as described above.

In the aforementioned manner, the connector 1 according to Embodiment 1 is equipped with the radially expandable balloon 20 that is arranged on the outer wall surface of the tube 10. Thus due to expansion or contraction of the balloon 20, attachment to or detachment from the vascular channel can be performed easily in a short period.

Moreover, the connector 1 according to Embodiment 1 is configured so as to sandwich the vascular channel between the outer wall surface of the balloon 20 and the inner wall surface of the tubular body 30. Therefore, leakage of the perfusion solution from the connector 1, falling out of the connector 1 from the vascular channel, and damage by the connector 1 to the vascular channel tissue can be prevented.

The fluid supply system 100 according to Embodiment 1 is equipped with the control device 113 that controls the fluid supply unit 111 to maintain the fluid pressure within the balloon 20 at the setting value on the basis of the measurement results of the pressure measurement unit 112. Therefore, the leakage of the perfusion solution, the falling out of the connector 1 from the vascular channel, and damage by the connector 1 to the vascular channel tissue can be effectively prevented.

Embodiment 2

A connector 2 according to Embodiment 2 of the present disclosure is described with reference to FIG. 5. Although per the connector 1 according to Embodiment 1 the tubular body 30 is a simple cylindrical shape, a concavity 31, corresponding to the shape of the balloon 20, may be provided in the interior wall portion of the tubular body 30.

Figure 5:
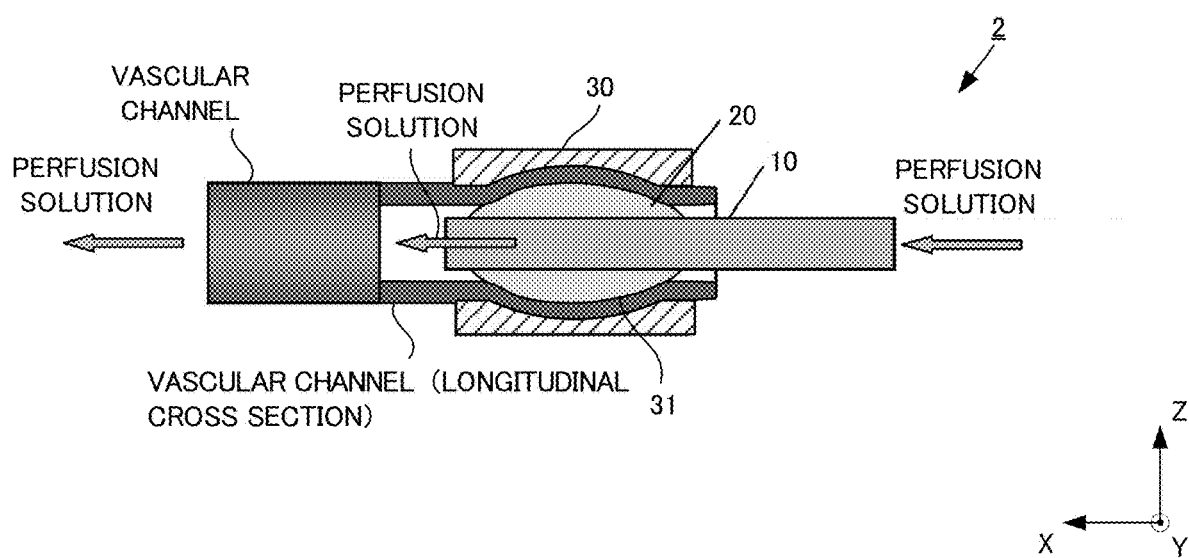
FIG. 5 is a cross-sectional view illustrating a connector according to Embodiment 2 of the present disclosure.

FIG. 5 is a cross-sectional view taken along the connector 2 according to Embodiment 2 in the longitudinal axis direction. To facilitate understanding in FIG. 5, a portion of the vascular channel, and the balloon 20 and the tubular body 30, are illustrated in cross section. The interior wall portion of the tubular body 30 has a largest internal diameter at the center in the longitudinal axis direction, and is provided with a concavity 31 that is formed so as to gradually narrow toward both end portions in the longitudinal axis direction. When the balloon 20 is expanded, the vascular channel is pressed against the concavity 31 of the interior wall portion of the tubular body 30 by the balloon 20 expanded into the approximate spindle shape. Due to such pressing, falling out of the connector 2 from the vascular channel can be prevented.

Embodiment 3

A connector 3 according to Embodiment 3 of the present disclosure is described with reference to FIGS. 6A, 6B, and 6C. Although the tube 10, and the tubular body 30 are entirely separate bodies in Embodiment 1, the tubular body 30 may be moveably coupled to the tube 10.

Figure 6:
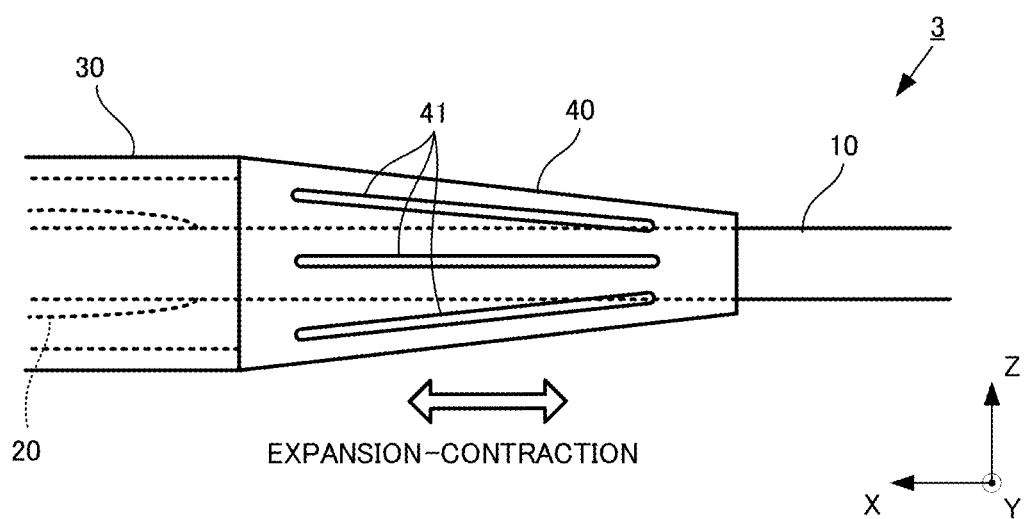
FIG. 6A is a magnified view of a periphery of a coupling member and illustrating a connector according to Embodiment 3 of the present disclosure.
FIG. 6B is a side view illustrating insertion into the vascular channel and illustrating the connector according to Embodiment 3 of the present disclosure.
FIG. 6C is a side view illustrating connecting to the vascular channel and illustrating the connector according to Embodiment 3 of the present disclosure.
Figure 6B:
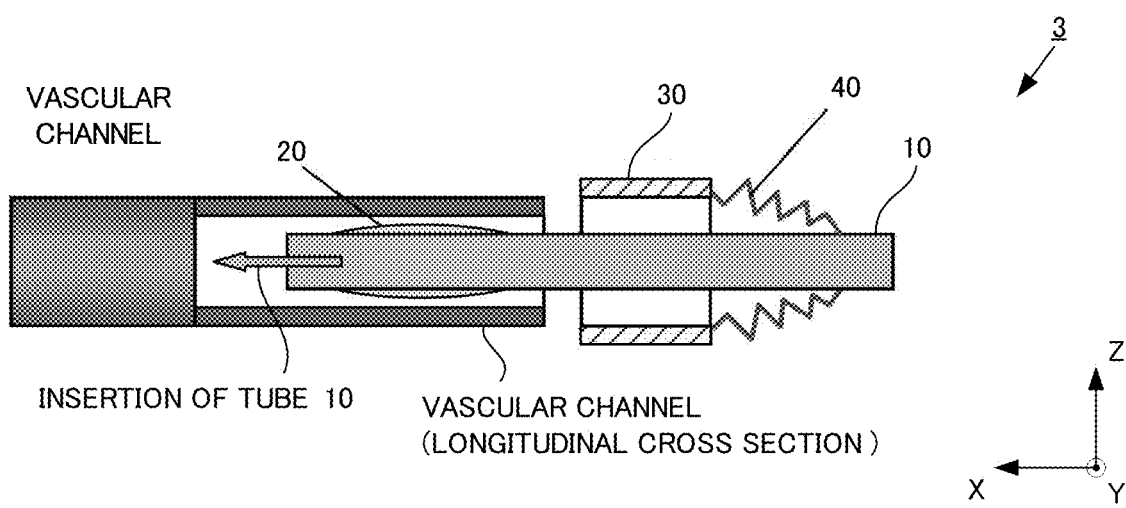
Figure 6C:
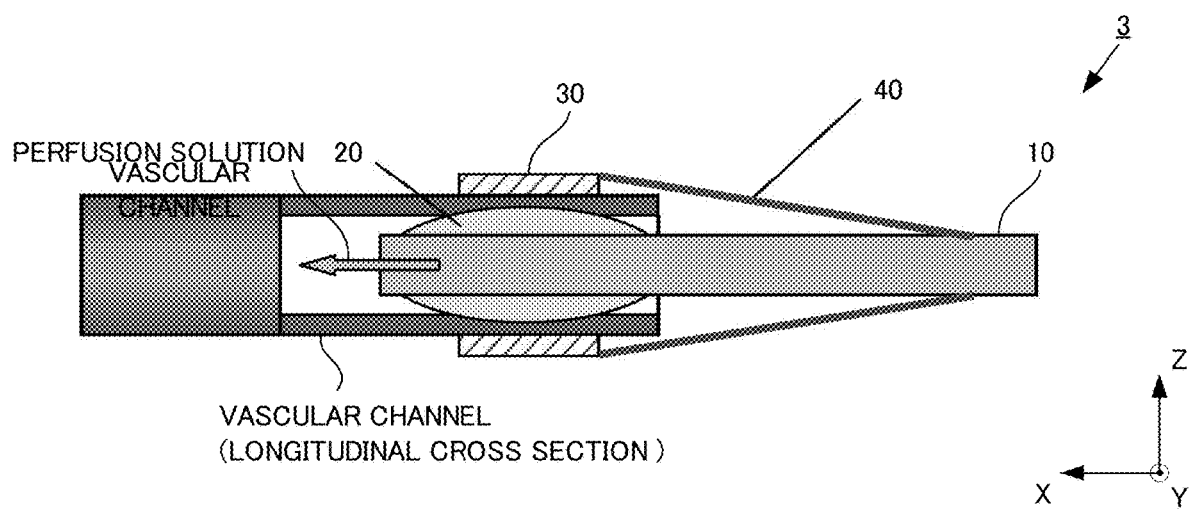

FIGS. 6A, 6B, and 6C illustrate the connector 3 according to Embodiment 3, in which FIG. 6A is a magnified view of a periphery of a coupling member 40, FIG. 6B is a side view illustrating insertion of the tube 10 into the vascular channel, and FIG. 6C is a side view illustrating connection of the connector 3 to the vascular channel. To facilitate understanding, FIGS. 6B and 6C illustrate in cross section a portion of the vascular channel, as well as the balloon 20, the tubular body 30, and the coupling member 40. As illustrated in FIG. 6A, the connector 3 is equipped with the coupling member 40 that couples together the tube 10 and the tubular body 30 such that the tubular body 30 is moveable with respect to the tube 10.

The coupling member 40 is an example of the coupling means for coupling together the tube 10, and the tubular body 30. The coupling member 40 is equipped with a tubular member formed from elastic material and a plurality of slits 41 formed in the longitudinal axis direction of the tubular member. In the coupling member 40, a distal part is fixed to a base part of the tubular body 30, and a base part of the coupling member 40 is fixed to the outer wall portion of the tube 10. The coupling member 40 is formed from a material such as an elastic material, and is further preferably formed from cloth, rubber, elastomer, or the like soft material. The coupling member 40 is configured to be elastically deformable so as to shrink and stretch in the longitudinal axis direction, and therefore the tubular body 30 can move in the longitudinal axis direction relative to the tube 10. The coupling member 40 is formed so as to dispose the tubular body 30 around the balloon 20 when the coupling member 40 is most extended.

When the tube 10 is inserted in the vascular channel, as illustrated in FIG. 6B, the tubular body 30 is moved the most to the base side (right side), and the tube 10 is inserted into the vascular channel until the balloon 20 is entirely in the vascular channel. Due to the lack of presence of the tubular body 30 surrounding the balloon 20, the tube 10 is easily inserted into the vascular channel. Next, after completion of the insertion operation, as illustrated in FIG. 6C, the tubular body 30 is moved to the limit of the distal side, that is, the left side. At this time, although the balloon 20 is hidden in the interior of the vascular channel, by simply moving the tubular body 30 to the distal side, the tubular body 30 can be disposed so as to cover the periphery of the balloon 20. When the balloon 20 expands in this state, connection to the vascular channel is completed.

In the aforementioned manner, the connector 3 according to Embodiment 3 is equipped with the coupling member 40 that couples between the tube 10, and the tubular body 30 so that the tubular body 30 is moveable relative to the tube 10. Thus the tube 10 can be easily inserted into the vascular channel by just moving the tubular body 30 to the base side. Moreover, after insertion of the tube 10 into the vascular channel, even though the resultant state is the state in which the balloon 20 is hidden by the vascular channel, the tubular body 30 can be disposed so as to cover the perimeter of the balloon 20, and thus the tubular body 30 is easily positioned.

Embodiment 4

A connector 4 according to Embodiment 4 of the present disclosure is described with reference to FIGS. 7A and 7B. Although the coupling member 40 in Embodiment 3 is the cylindrical shaped member equipped with the plurality of slits 41, the coupling member 40 may be a tubular cover configured so as to cover and seal a portion of the tube 10.

Figure 7A:
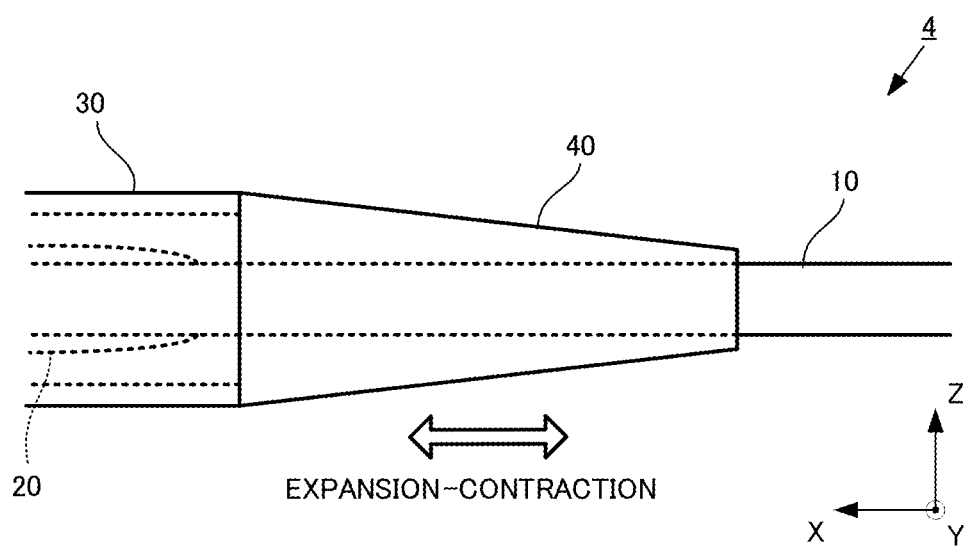
FIG. 7A is a magnified view of a periphery of a coupling member and illustrates a connector according to Embodiment 4 of the present disclosure.
Figure 7B:
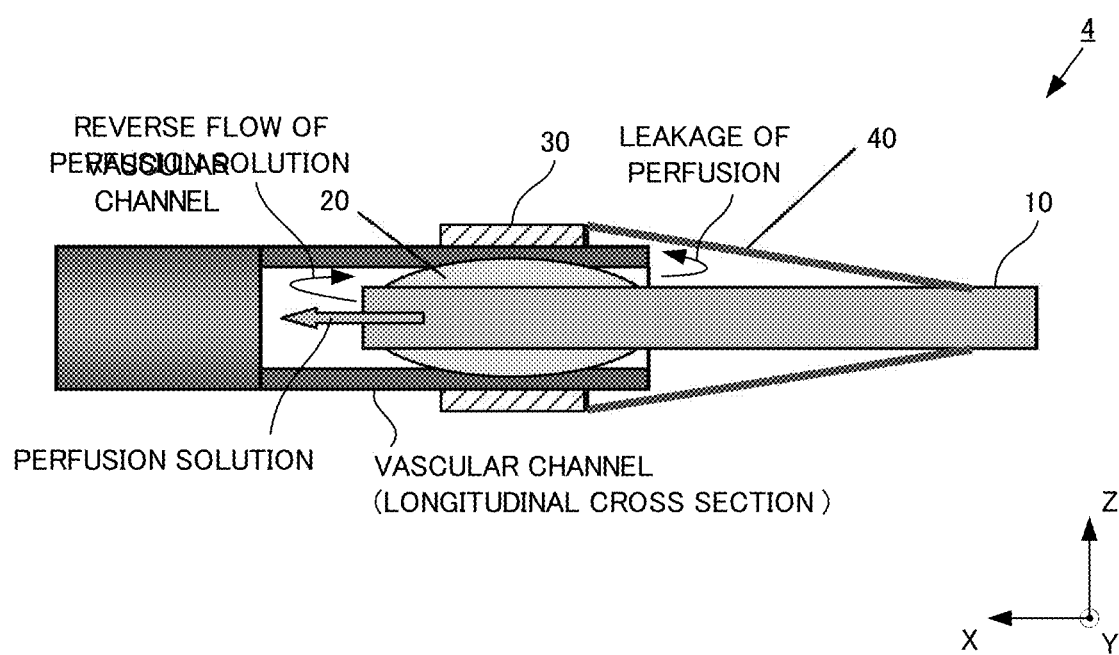
FIG. 7B is a side view illustrating connecting to the vascular channel and illustrating the connector according to Embodiment 4 of the present disclosure.

FIG. 7A is a magnified view of the periphery of the coupling member 40, and FIG. 7B is a cross-sectional view illustrating flow of the perfusion solution when the connector 4 is connected to the vascular channel. In FIG. 7B to facilitate understanding, a portion of the vascular channel, as well as the balloon 20, the tubular body 30, and the coupling member 40, are illustrated in cross section. The coupling member 40 entirely covers, so as to seal, a portion of the outer wall portion of the tube 10, and is a tubular cover that is entirely lacking in slits, holes, or the like that would allow passage of a fluid. The distal part of the coupling member 40 closely contacts and fixes to the base part of the tubular body 30, and the base part of the coupling member 40 closely contacts and fixes to the outer wall portion of the tube 10. Thus the coupling member 40 forms a sealed space in the interior of both the tube 10, and the tubular body 30.

The connector 4, by close contact between the interior wall portion of the vascular channel and the outer wall portion of the balloon 20, prevents leakage of the perfusion solution. Due to sealing of the space between the outer wall portion of the vascular channel and the interior wall portion of the tubular body 30, the perfusion solution cannot pass through the coupling member 40, and thus even if the perfusion solution leaks from between the vascular channel and the balloon 20 as indicated by an arrow of FIG. 7B, the leaked perfusion solution can be confined. Due to the achievement of sealing at multiple locations when connected to the vascular channel, the connector 4 in this manner can more effectively prevent leakage of the perfusion solution Embodiment 5

A connector 5 according to Embodiment 5 of the present disclosure is described with reference to FIGS. 8A, 8B, 9A, and 9B. Although the balloon 20 is arranged at the outer wall portion of the tube 10 in Embodiment 1, a configuration may be used in which the balloon 20 is arranged on the interior wall portion of the tubular body 30, and the balloon 20 expands toward the tube 10.

In the case of providing of the balloon 20 on the outer wall portion of the tube 10 as in the connector 1 according to Embodiment 1, the vascular channel is pressed outwardly in the radial direction by expansion of the balloon 20. Thus a region exists, as illustrated in FIG. 2A, in which the fluid is stagnant between the distal part of the tube 10 and the interior wall portion of the vascular channel. In the case of use of the connector 1 for a blood circulation circuit, a blood clot can possibly form in the stagnant region, and elimination of the region where the fluid is stagnant is desirable.

Figure 8A:
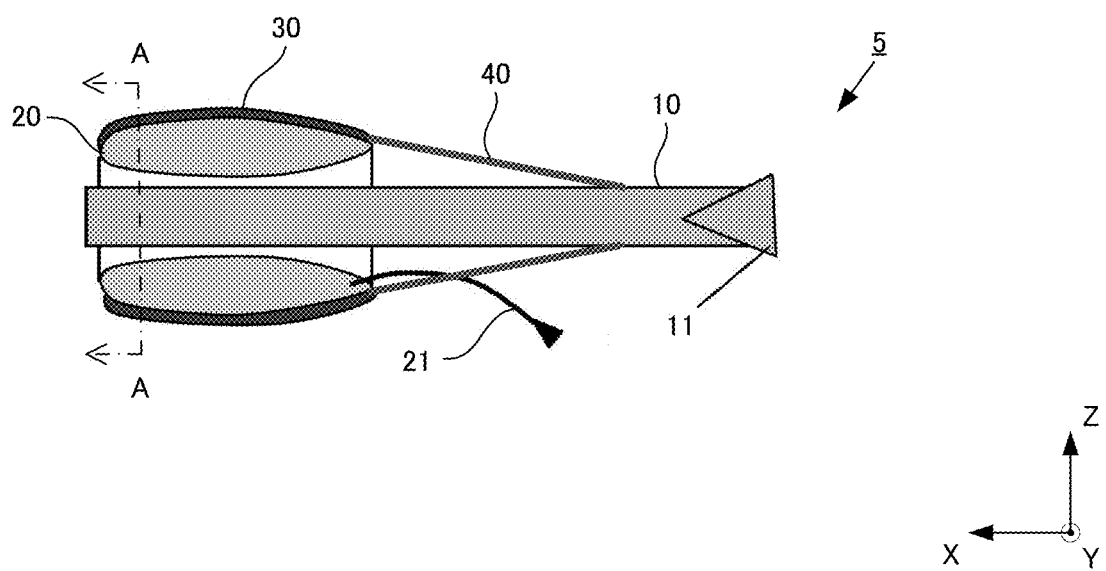
FIG. 8A is a side view illustrating a connector according to Embodiment 5 of the present disclosure.
Figure 8B:
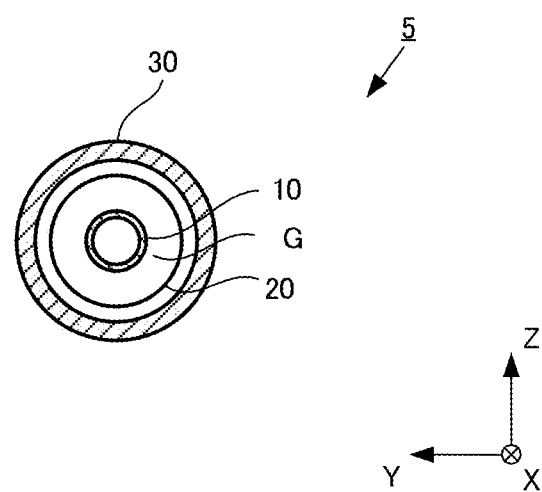
FIG. 8B is a cross-sectional view taken at line A-A of the connector illustrated in FIG. 8A and illustrates the connector according to Embodiment 5 of the present disclosure.

FIG. 8A is a side view of the connector 5 according to Embodiment 5, and FIG. 8B is a cross-sectional view taken along line A-A of the connector 5 illustrated in FIG. 8A. In FIG. 8A, the balloon 20, the tubular body 30, and the coupling member 40 are illustrated in cross section to facilitate understanding. The connector 5 according to Embodiment 5 is equipped with the tube 10 that is insertable into the vascular channel, the tubular body 30 that is arrangeable in the interior of the tube 10, the balloon 20 that is arranged on the interior wall portion of the tubular body 30 and is radially expandable, and a coupling member 40 for coupling between the tube 10, and the tubular body 30 such that the tubular body 30 is movable in the longitudinal axis direction relative to the tube 10.

The balloon 20 is formed from a tubular membrane-like member. The distal part and the base part of the balloon 20 are each fixed in close contact with the interior wall portion of the tubular body 30. The balloon injection tube 21 is connected to the balloon 20, and the fluid is supplied from the balloon injection tube 21 into the balloon 20.

Figure 9A:
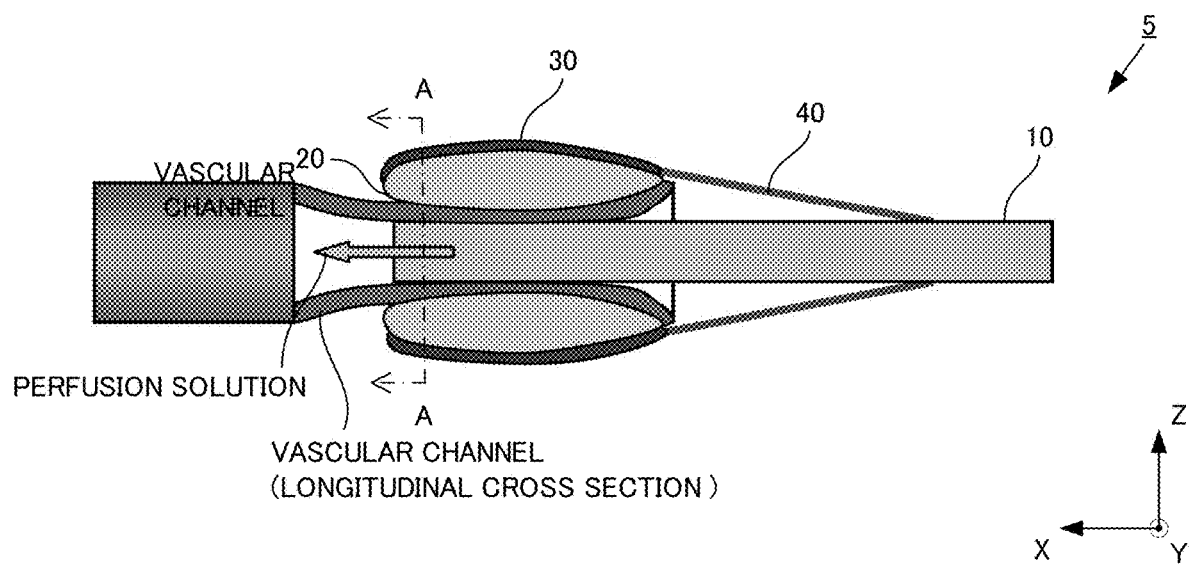
FIG. 9A illustrates connecting of the connector of FIGS. 8A and 8B to the vascular channel and is a side view.
Figure 9B:
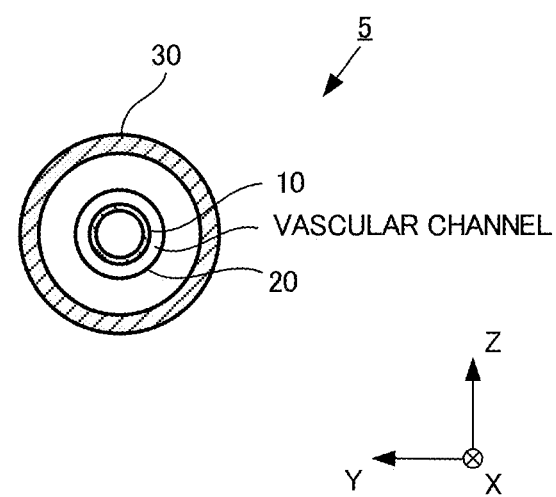
FIG. 9B illustrates connecting of the connector of FIGS. 8A and 8B to the vascular channel and is a cross-sectional view taken at line A-A of the connector illustrated in FIG. 9A.

FIGS. 9A and 9B are cross-sectional views illustrating attachment of the connector 5 to the vascular channel, and FIG. 9B is a cross-sectional view taken along line A-A of the connector 5 illustrated in FIG. 9A. In FIG. 9A to facilitate understanding, part of the vascular channel, as well as the balloon 20, the tubular body 30, and the coupling member 40, are illustrated in cross section. Due to expansion of the balloon 20 arranged on the interior wall portion of the tubular body 30 in the inward direction, the connector 5 sandwiches the vascular channel between the outer wall portion of the tube 10 and the interior wall portion of the balloon 20. Due to the lack of occurrence in the connector 5 of the stagnant region of the fluid between the distal part of the tube 10 and the vascular channel, the connector 5 can prevent the occurrence of a blood clot when the connector 5 is used in the blood circulation circuit.

Further, a groove, protuberance, irregularity, or the like may be arranged in the outer wall portion of the tube 10. The groove, protuberance, irregularity, or the like arranged in the outer wall portion of the tube 10 causes an increase in frictional force between the outer wall portion of the tube 10 and the vascular channel, and thus can further prevent falling out of the connector 5 from the vascular channel.

In the aforementioned manner, the connector 5 according to the Embodiment 5 is equipped with: the tubular body 30 having the inner wall surface that from the outside, with the outer wall surface of the tube 10 from the inside, is capable of sandwiching the vascular channel when the tube 10 is disposed in the interior of the vascular channel, and the balloon 20 that is arranged on the inner wall surface of the tubular body 30 and is radially expandable. Due to such configuration, even when the connector 5 is used in the blood circulation circuit, the generation of blood clots caused by stagnant blood can be prevented.

Embodiment 6

A connector 6 according to Embodiment 6 of the present disclosure is described with reference to FIG. 10. Unlike the connector 5 according to Embodiment 5, in Embodiment 6 the a concavity 12 is provided, in the distal side of the outer wall portion of the tube 10, that corresponds to the shape of the balloon 20 when expanded.

Figure 10:
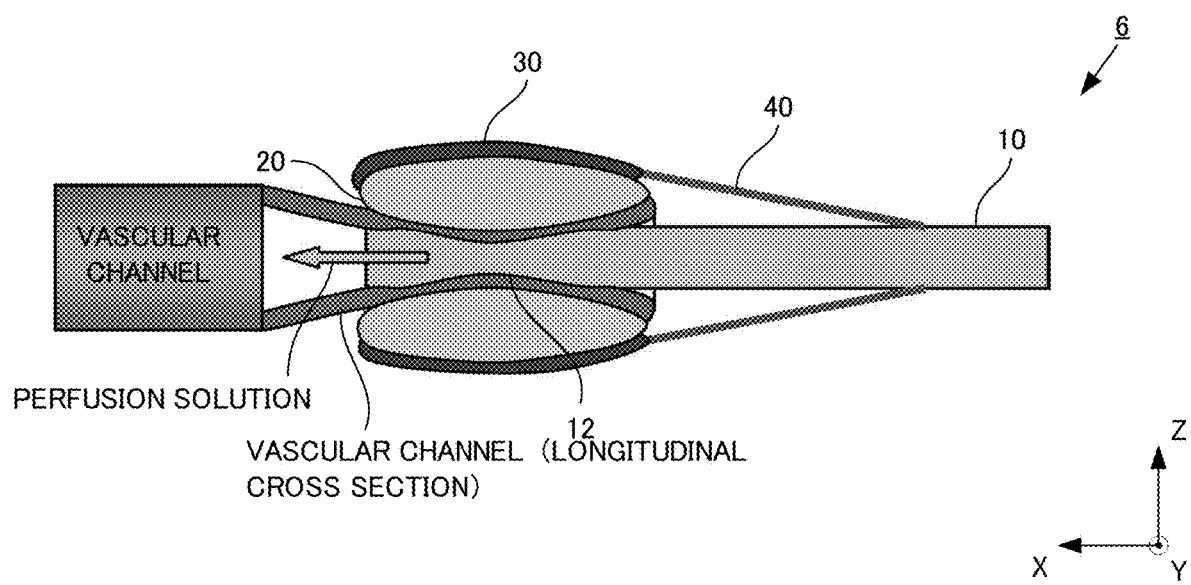
FIG. 10 is a side view illustrating a connector according to Embodiment 6 of the present disclosure.

FIG. 10 is a cross-sectional view of the connector 6 according to Embodiment 6. To facilitate understanding in FIG. 10, part of the vascular channel, as well as the balloon 20, the tubular body 30, and the coupling member 40, are illustrated in cross section. The concavity 12 is provided in the tube 10 and is formed continuously in the circumferential direction at the distal side of the outer wall portion. The concavity 12 is formed to match the shape of the interior wall portion of the balloon 20 when expanded. Thus when the vascular channel is sandwiched between the interior wall portion of the balloon 20 and the outer wall portion of the tube 10, and then the balloon 20 is expanded, the vascular channel compressed by the balloon 20 fits into the concavity 12 of the tube 10. Such fitting can prevent falling out of the connector 6 from the vascular channel.

Embodiment 7

A connector 7 according to Embodiment 7 of the present disclosure is described with reference to FIGS. 11A and 11B. In Embodiment 7, the tubular body 30 includes a plurality of members, and thus differs from the connectors 1 to 6 according to Embodiments 1 to 6. Further, the term "separable" does not only refer to the case in which the members are completely separable, but also include the case in which some parts of the members are mutually connected and the other parts of the members are mutually separable.

Figure 11A:
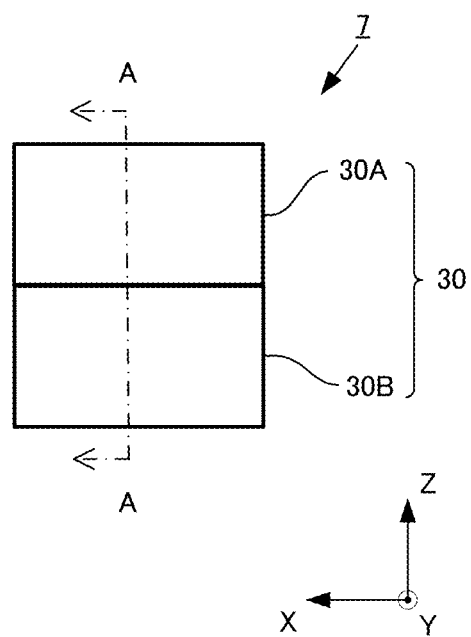
FIG. 11A is a side view illustrating a connector according to Embodiment 7 of the present disclosure.
Figure 11B:
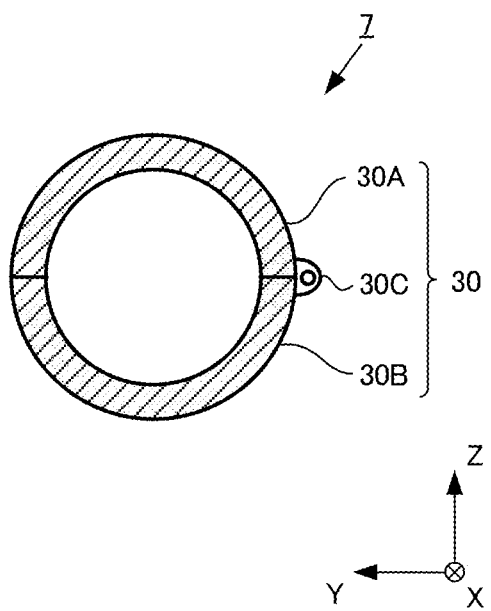
FIG. 11B is a side cross-sectional view taken at line A-A of a tubular body illustrated in FIG. 11A.

FIGS. 11A and 11B illustrate the connector 7 equipped with the tubular body 30 configured to be separable. Illustration of the tube 10 and the balloon 20 is omitted from FIGS. 11A and 11B to facilitate understanding. The tubular body 30 is equipped with a first piece part 30A and a second piece part 30B that are semicircular in cross section and are configured to be mutually separable. The first piece part 30A and the second piece part 30B are rotatably coupled via a hinge 30C. The tubular body 30 is equipped with a fixing means for fixing such that the first piece part 30A and the second piece part 30B do not rotate relative to each other. The fixing means, for example, is a hook and an engagement hole capable of mutual engagement and arranged at the side opposite to the hinge 30C. Further, the first piece part 30A and the second piece part 30B may be fixed together by a fixing means as a separate body such as a band formed from elastic material, for example.

At the site of an actual organ transplant, connection of the connector 7 sometimes occurs after cutting of a T-shaped incision by cutting lengthwise into the distal part of the vascular channel. Moreover, sometimes the distal part of the vascular channel has a knobby shaped swelling, or a clump of fat is attached to the distal part. In the case of use of the tubular body 30 according to Embodiments 1 to 6, cases can be envisioned in which the tubular body 30 cannot be attached due to prevention by the T-shaped vascular channel, the knobby shaped swelling, the clump of fat attached to the vascular channel, or the like. However, in the case of providing of tubular body 30 with the separable configuration as illustrated in FIGS. 11A and 11B, even in the presence of the T-shaped vascular channel, the knobby shaped swelling, the clump of fat, or the like, the tubular body 30 can be separated so that the vascular channel is sandwiched, and thus the connector 7 can be mounted on the desired portion of the vascular channel.

Embodiment 8

The connector 8 according to Embodiment 8 of the present disclosure is described with reference to FIGS. 12A, 12B, and 12C. Embodiment 8 differs from the connector 7 according to Embodiment 7 in including the tubular body 30 that is adjustable in width in the Y axis direction.

Figure 12A:
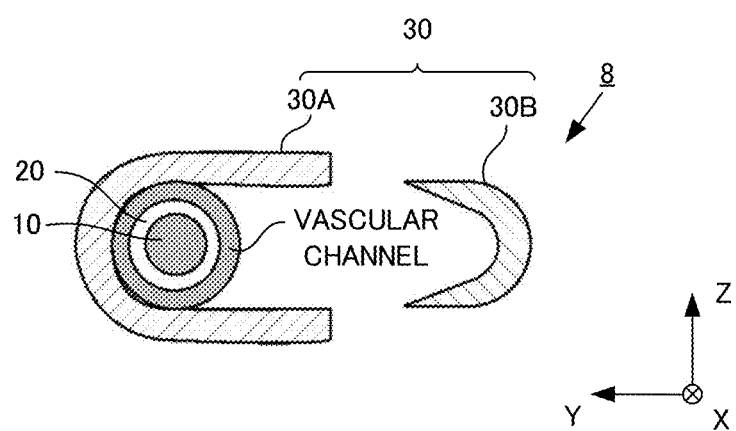
FIG. 12A is a side cross-sectional illustrating one member of a tubular body and illustrates a connector according to Embodiment 8 of the present disclosure.
Figure 12B:
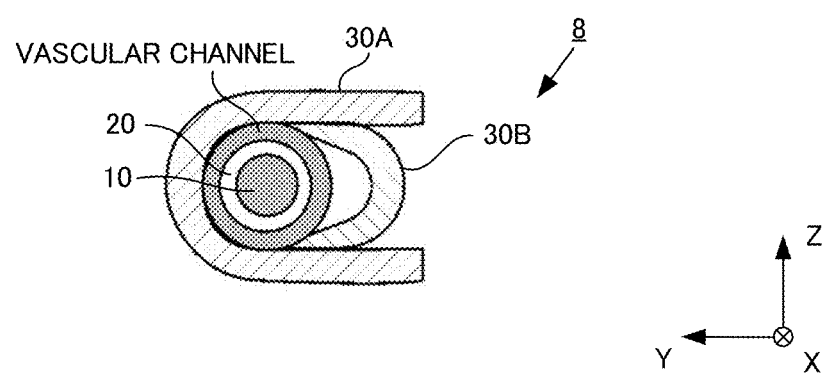
FIG. 12B is a side cross-sectional view illustrating attachment of one member of the tubular body to the vascular channel and illustrates the connector according to Embodiment 8 of the present disclosure.
Figure 12C:
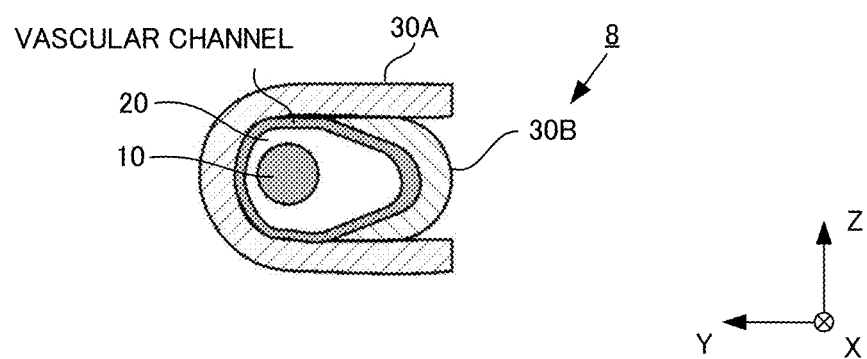
FIG. 12C is a side cross-sectional view illustrating expansion of a balloon toward the tubular body and illustrates the connector according to Embodiment 8 of the present disclosure.

FIGS. 12A, 12B, and 12C are side cross-sectional views illustrating the connector 8 equipped with the tubular body 30 that is configured to be separable into two members; FIG. 12A illustrates mounting of one of the members of the tubular body 30 on the vascular channel; FIG. 12B illustrates mounting of the other member of the tubular body 30; and FIG. 12C illustrates expansion of the balloon 20 toward the integrated tubular body 30. The tubular body 30 is equipped with a first piece part 30A having an opening extending in the length-wise direction (X axis direction) and having a side cross-sectional shape that is U shaped, and a second piece part 30B capable of mounting from the width direction (Y axis direction) of the first piece part 30A so as to cover the opening of the first piece part 30A.

The first piece part 30A is formed such that the interior surfaces of both end parts opposing each other and extending in the Y axis direction are mutually parallel, and the second piece part 30B is formed such that the outer surfaces of both of the pair of end parts extending in the Y axis direction are mutually parallel. In the pair of both end inner surfaces of the first piece part 30A and the pair of both end outer surfaces of the second piece part 30B, a non-illustrated ratchet mechanism is arranged for limiting movement (+Y axis direction) of the second piece part 30B relative to the first piece part 30A.

More specifically, on pair of end inner surfaces of the first piece part 30A, multiple hill-shaped teeth are formed that extend in the Y axis direction. Moreover, on the pair of end outer surfaces of the second piece part 30B are formed tabs that engage the multiple teeth of the first piece part 30A and each project in the radial direction. The distal side of the multiple teeth of the first piece part 30A is formed such that, when the second piece part 30B is pressed into the first piece part 30A, the first piece part 30A or the second piece part 30B deforms such that the tabs of the second piece part 30B can form an angle that allows the second piece part 30B to override. Moreover, the tabs of the second piece part 30B are formed at a steep angle, such as by being formed at an angle perpendicular with respect the pair of both end portions of the first piece part 30A, so that the second piece part 30B is not overcome when the base side of the teeth of the first piece part 30A are pulled in the direction of pulling out of the second piece part 30B from the first piece part 30A.

The first piece part 30A and the second piece part 30B are each formed from elastically deformable material. Thus when the first piece part 30A and the second piece part 30B are separated, the second piece part 30B can be pulled out and removed from the first piece part 30A by causing deformation of either the first piece part 30A or the second piece part 30B.

The method of use of the connector 8 is described next. Firstly, the user arranges the tube 10 in the interior of the first piece part 30A with the vascular channel arranged above the balloon 20. Next, the user mounts the second piece part 30B on the first piece part 30A so as to cover the balloon 20 around which the vascular channel is arranged. At this time, the second piece part 30B can be fixed at a desired position along the Y axis relative to the first piece part 30A while taking in to account factors such as outer diameter, wall thickness, or the like of the vascular channel.

Next, the user presses the vascular channel against the tubular body 30 by causing the balloon 20 to expand. At this time, even through pressure is received from the expanded balloon 20, due to engagement between the teeth of the first piece part 30A and the tabs of the second piece part 30B, the second piece part 30B does not separate from the first piece part 30A. The connection between the connector 8 and the vascular channel is completed by the aforementioned steps.

Example 1

Experiments, and result thereof, executed to verify the characteristics of the connectors 1 and 2 of the aforementioned Embodiments 1 and 2 are described next.

Figure 13A:
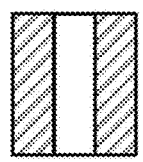
FIG. 13A illustrates cross-sectional views of cross sections of various tubular bodies in Example 1.
Figure 13A:
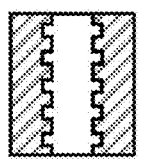
Figure 13A:
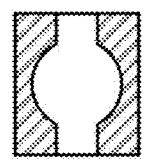
Figure 13A:
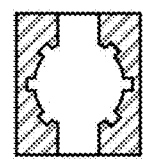
Figure 13A:
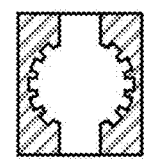

FIG. 13A illustrates cross sections of tubular bodies 30 used in the present verification. The tubular body 30 of a first cross-sectional shape is a tubular body 30 for which the inner wall surface is smooth. In the tubular body 30 of the second cross-sectional shape, the first cross-sectional shape undergoes groove processing to form irregularities in the inner wall surface. In the tubular body 30 of the third cross-sectional shape, the central portion of the inner wall surface of the tubular body 30 is concavely formed. The tubular body 30 of the fourth cross-sectional shape has a combination of the tubular bodies 30 of the second cross-sectional shape and the third cross-sectional shape, the tubular body 30 of the fifth cross-sectional shape has a combination of the tubular bodies 30 of the second cross-sectional shape and the third cross-sectional shape, and the tubular body 30 of the fifth cross-sectional shape has a greater number of grooves than the tubular body 30 of the fourth cross-sectional shape.

A thin rubber tube was prepared to simulate the vascular channel, and the rubber tube was coated with silicone oil of 50 cS viscosity in order to reproduce slipperiness of the vascular channel. This rubber tube was connected to the connector according to an embodiment, and tensile testing was performed until the rubber tube pulled out. The maximum pulling force during pulling out of the rubber tube was defined as the pull-out force T, and the pull-out force T was evaluated as higher with greater difficulty of pulling out of the connector.

Figure 13B:
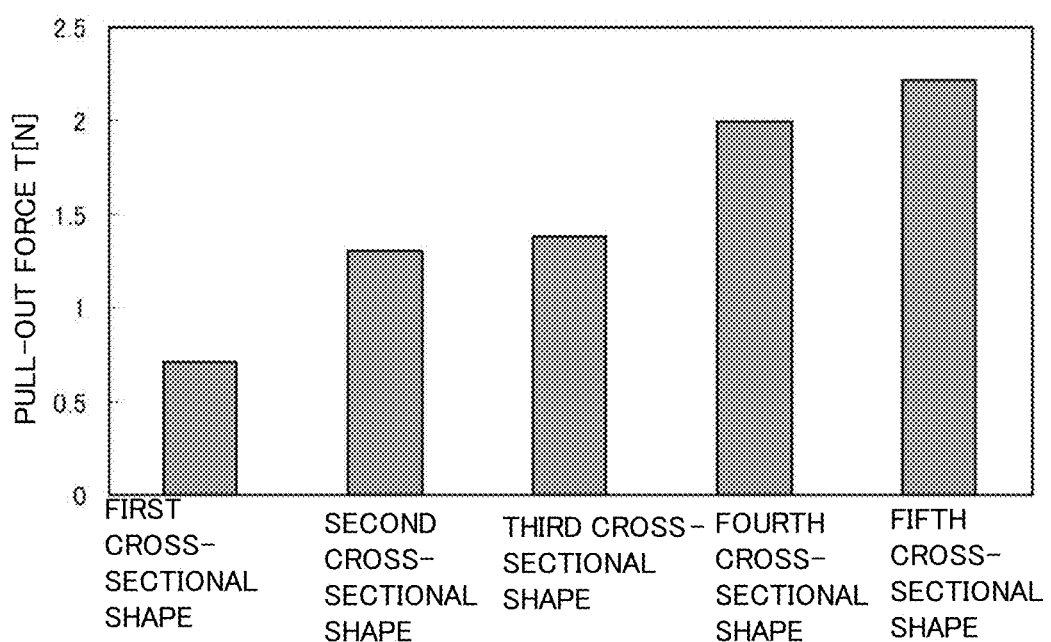
FIG. 13B is a graph illustrating measurement results of pull-out force for each tubular body in Embodiment 1.

FIG. 13B illustrates measurement results of the pull-out force T corresponding to the various tubular bodies 30. The pull-out force T increased, in order, as that of the first cross-sectional shape, the second cross-sectional shape, the third cross-sectional shape, the fourth cross-sectional shape, and the fifth cross-sectional shape.

Due to this result, the falling out of the connector from the vascular channel can be understood to be preventable by both the concavity arranged at the central portion of the inner wall surface of the tubular body 30 and the irregularity-shaped grooves arranged in the inner wall surface of the tubular body 30. Moreover, the falling out of the connector from the vascular channel can be understood to be preventable by the combination of the concavity and the irregularity-shaped grooves, and the falling out of the connector from the vascular channel can be understood to be increasingly preventable with increase in the number of the irregularity-shaped grooves.

Next, the connector 2 according the aforementioned Embodiment 2 was used for an experiment testing perfusion of the vascular channel of a pig liver. In this experiment, the connector 2 equipped with the tubular body 30 of the fourth cross-sectional shape was used, and the vascular channel of the pig liver was perfused for 4 hours. The vascular channel tissue after perfusion was checked visually, and maintenance of the vascular channel tissue in good condition could be confirmed.

This result indicates that the connector 2 according to the aforementioned Embodiment 2 does not cause damage to living body tissue.

Example 2

Next, an experiment and result thereof are described in order to verify characteristics of the connector 8 according to the aforementioned Embodiment 8.

Firstly, a T-shaped incision was formed in the distal side of a vascular channel to which a clump of fat or the like was attached, and the vascular channel and the connector 8 were connected together. Thereafter, perfusion of the vascular channel from the connector 8 was started, and perfusion testing was performed.

After completion of the perfusion testing, the connector 8 was removed from the vascular channel, and when the vascular channel was visually inspected, the vascular channel was seen to not be damaged, and the vascular channel was confirmed to have sufficient effective length for organ transplantation by a physician. Moreover, the mounting of the connector 8 on the vascular channel by the physician was performed in a short period, and the mounting operation was easy.

Due to the aforementioned results, the connector 8 can be confirmed to be useful as a measure for supplying the perfusion solution to the vascular channel of organs for transplantation that have individual differences.

The present disclosure is not limited to the aforementioned embodiments, and modifications as described below are possible.

Modified Examples

In the aforementioned embodiments, although the balloon injection tube 21 connected to the balloon 20 is arranged as a means for supplying the fluid to the balloon 20, the present disclosure is not limited to such configuration. For example, in addition to the tubular path for supply of the perfusion solution, the tubular path may be arranged in the interior of the tube 10 to supply the fluid to the interior of the balloon 20.

In the aforementioned embodiments, although the surface of the balloon 20 is smooth, the present disclosure is not limited to such configuration. For example, providing of irregularities or surface roughening may be performed on the surface of the balloon 20 to prevent slippage.

Although the expanded balloon 20 is approximately spindle-shaped in the aforementioned Embodiments 1 to 4, and the balloon 20 is approximately cylindrical-shaped in the aforementioned Embodiment 5 and 6, the present disclosure these is not limited to such configurations. The shape of the expanded balloon may be freely selected, and for example, this shape may be spherical, cylindrically-shaped, polygonal column-shaped, or the like.

Although the coupling member 40 is equipped with the tubular member in the aforementioned embodiments, the present disclosure is not limited to such configuration. As long as can be coupling member 40 can couple such that the tube 10, and the tubular body 30 are moveable relative to each other, the coupling member 40 may have any shape, such as a string-shaped, bellows-shaped, or spiral-shaped member. Moreover, the coupling member 40 may include a spring member such as a leaf spring, coil spring, or the like.

In the aforementioned embodiments, although the coupling member 40 is equipped with a fixing mechanism for fixing of position of the tube 10 relative to the tubular body 30, the present disclosure is not limited to such configuration. A fixing mechanism may be provided that fixes the tubular body 30 relative to the tube 10 when the tubular body 30 is moved furthest to the distal side and/or furthest to the base side.

Although in the aforementioned embodiments the balloon fluid supply device 110 is a device that maintains fluid pressure within the balloon 20 at a constant pressure, the present disclosure is not limited to such configuration. For example, the balloon fluid supply device 110 may be a device such as a syringe that, by operation by the user, is capable of supplying the perfusion solution into the balloon 20.

Although the perfusion solution supply device 120 in the aforementioned embodiments is a device that supplies the perfusion solution to the vascular channel at a fixed flow rate, the present disclosure is not limited to such configuration. For example, the perfusion solution supply device 120 may be a device such as a syringe that, by operation by the user, is capable of supplying the fluid into the balloon.

Figure 14A:
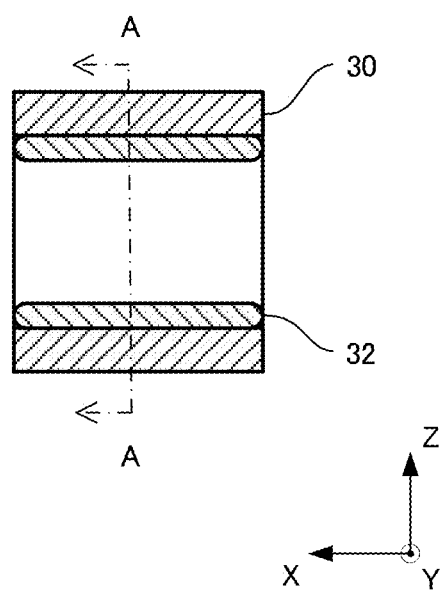
FIG. 14A is a vertical cross-sectional view illustrating the tubular body fixed by an elastic member to an interior wall portion.
Figure 14B:
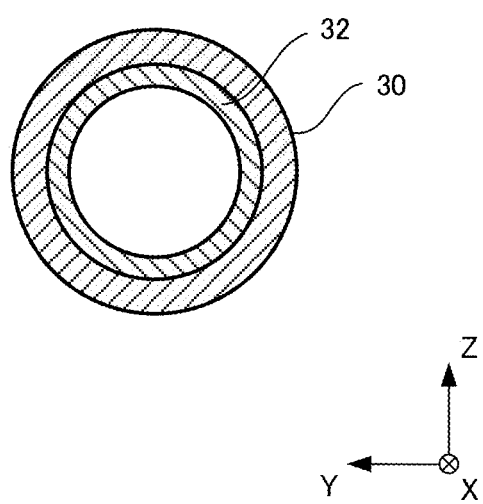
FIG. 14B is a side cross-sectional view taken along line A-A of the tubular body illustrated in FIG. 14A.

Although the interior wall portion of the tubular body 30 directly contacts the vascular channel in the configurations of the aforementioned Embodiments 1 to 4, the present disclosure is not limited to such configurations. For example, the cylindrically shaped elastic member 32 may fixed by a means such as attachment to the interior wall portion of the tubular body 30 as illustrated in FIGS. 14A and 14B. The elastic member 32 may be formed from an elastic material such as rubber, elastomers, polyurethanes, or the like that is capable of easily deforming to conform to the shape of the vascular channel when the vascular channel is pressed by the balloon 20. When the vascular channel is pressed by the outer wall portion of the expanded balloon 20 and is pressed against the elastic member 32, the elastic member 32 deforms to closely contact and conform to the vascular channel, and damage to the vascular channel due to connection of the connector 1 to 4 is further prevented.

Although in the aforementioned Embodiment 8 the ratchet mechanism is used as the fixing means for fixing together the first piece part 30A and the second piece part 30B, the present disclosure is not limited to such configuration. For example, at least one of the outer surfaces of the pair of end portions of the second end part 30B and the inner surfaces of the pair of end portions of the first piece part 30A may undergo surface processing to increase frictional resistance by forming concavities, convexities, irregularities, grooves, or roughness, and the first piece 30A and the second piece part 30B may be thus fixed together.

Moreover, a configuration may be used by which spaces of the inner surfaces occurring at the pair of end portions of the second piece parts 30B are larger than respective spaces of the outer surfaces occurring at the pair of end portions of the first piece part 30A. In this case, either the first piece part 30A or the second piece part 30B may deform elastically, that is, the second piece part 30B may mount on the first piece part 30A such that the first piece part 30A is compressed or the second piece part 30B is expanded. In this case, a pressing force is generated between the first piece part 30A and the second piece part 30B, thereby more strongly fixing the first piece part 30A and the second piece part 30B together.

In the aforementioned embodiments, the program for causing execution of the sealing-connecting processing of FIG. 4 is stored in the storage 113d of the balloon fluid supply device 110, although the present disclosure is not limited to such configuration. The program for causing execution of the aforementioned processing operations can be stored on computer-readable recording medium such as a flexible disk, a compact disk read-only memory (CD-ROM), a digital versatile disk (DVD), a magneto-optical (MO) disk, or the like, and the balloon fluid supply device 110 may be achieved that executes the aforementioned processing by the program recorded on the recording medium being installed on a computer.

In the aforementioned embodiments, although cases are described of use of the connectors 1 to 8 for the perfusion of the vascular channel of the organ, the present disclosure is not limited to such configuration. For example, the connectors 1 to 8 may be used in the case of connection of a blood vessel inside the body to an artificial heart, a dialysis apparatus, an artificial circulation device arranged external to the human body, or the like. Moreover, the connector 1 to 8 may be used in a technical field outside of the medical field.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

This application claims the benefit of Japanese Patent Application No. 2017-67202, filed on Mar. 30, 2017, the entire disclosure of which is incorporated by reference herein.

INDUSTRIAL APPLICABILITY

The connector and the fluid supply system of the present disclosure are useful for enabling attachment to and detachment from a soft tubular member, such as the vascular channel of a organ for transplant, in a short period without damage to the soft tubular member.

REFERENCE SIGNS LIST 1, 2, 3, 4, 5, 6, 7, 8 Connector
11 Tube
12 Connection member
12 Concavity
20 Balloon
21 Balloon injection tube
30 Tubular body
30A First piece part
30B Second piece part
30C Hinge
31 Concavity
32 Elastic member
40 Coupling member
41 Slit
100 Fluid supply system 110 Balloon fluid supply device
111 Fluid supply unit
112 Pressure measurement unit
113 Control device
113a Command receiver
113b Display
113c Communication unit
113d Storage
113e Controller
120 Perfusion solution supply device
G Gap
T Pull-out force

The invention claimed is:

1. A connector comprising:
a tube configured to be arranged in an interior of a soft tubular member;
a tubular body having an inner wall surface configured to, together with an outer wall surface of the tube, sandwich the soft tubular member when the tube is arranged in the interior of the soft tubular member;
a balloon, configured to be arranged on the outer wall surface of the tube or the inner wall surface of the tubular body, and radially expand for performing sealing (i) between the soft tubular member and the inner wall surface of the tubular body and (ii) between the soft tubular member and the outer wall surface of the tube; and
wherein the soft tubular member is configured to be pressed by the balloon against the inner wall surface of the tubular body or the outer wall surface of the tube.

2. The connector according to claim 1, wherein
the balloon is disposed so as to surround the outer wall surface of the tube or the inner wall surface of the tubular body in the circumferential direction, and when expanded, to perform sealing between the soft tubular member and the inner wall surface or the outer wall surface.

3. The connector according to claim 1, wherein
a concavity is formed in the inner wall surface of the tubular body at a part contacting the expanded balloon, or a concavity is formed the outer wall surface of the tube at a part contacting the expanded balloon.

4. The connector according to claim 1, wherein
a groove, a protuberance, or an unevenness for suppressing slippage of the soft tubular member is formed in the inner wall surface of the tubular body or the outer wall surface of the tube.

5. The connector according to claim 1, wherein
the balloon is arranged on the outer wall surface of the tube and is configured to radially expand toward the inner wall surface of the tubular body, and
the tubular body includes a plurality of members that are mutually separable, and are integrated into a single body by assembly.

6. The connector according to claim 1, further comprising:
coupling member for coupling together the tube and the tubular body such that the tubular body is movable relative to the tube.

7. The connector according to claim 6, wherein
the coupling member is formed so as to expand and contract with elastic deformability in a longitudinal axis direction of the tube.

8. The connector according to claim 6, wherein
the coupling member comprises (i) a tubular member formed from an elastic material and (ii) a plurality of slits formed in the longitudinal axis direction of the tubular member.

9. The connector according to claim 7, wherein
the coupling member is a tubular cover that is closely contactable with and fixable to the tube and the tubular body, and sealably encloses a fluid in an interior of the tubular cover.

10. A fluid supply system comprising:
the connector according to claim 1; and
a fluid supply device configured to supply a fluid into the interior of the soft tubular member and connectable to the connector.

11. The fluid supply system according to claim 10, further comprising:
a pump for supplying the fluid into the balloon;
a pressure sensor for measuring a fluid pressure within the balloon; and
control device for, based on a result of the measurement of the pressure sensor, controlling the pump to maintain the fluid pressure within the balloon at a set value.

12. A connector comprising:
a tube configured to be arranged in an interior of a soft tubular member;
a tubular body having an inner wall surface configured to, together with an outer wall surface of the tube, sandwich the soft tubular member when the tube is arranged in the interior of the soft tubular member;
a balloon, configured to be arranged on the outer wall surface of the tube or the inner wall surface of the tubular body, and radially expand for performing sealing (i) between the soft tubular member and the inner wall surface of the tubular body and (ii) between the soft tubular member and the outer wall surface of the tube; and
a concavity is formed in the inner wall surface of the tubular body at a part contacting the expanded balloon, or a concavity is formed the outer wall surface of the tube at a part contacting the expanded balloon.

13. A connector comprising:
a tube configured to be arranged in an interior of a soft tubular member;
a tubular body having an inner wall surface configured to, together with an outer wall surface of the tube, sandwich the soft tubular member when the tube is arranged in the interior of the soft tubular member;
a balloon, configured to be arranged on the outer wall surface of the tube or the inner wall surface of the tubular body, and radially expand for performing sealing (i) between the soft tubular member and the inner wall surface of the tubular body and (ii) between the soft tubular member and the outer wall surface of the tube; and
a coupling member for coupling together the tube and the tubular body such that the tubular body is movable relative to the tube.

14. The connector according to claim 13, wherein
the coupling member is formed so as to expand and contract with elastic deformability in a longitudinal axis direction of the tube.

15. The connector according to claim 13, wherein
the coupling member comprises (i) a tubular member formed from an elastic material and (ii) a plurality of slits formed in the longitudinal axis direction of the tubular member.

16. The connector according to claim 14, wherein the coupling member is a tubular cover that is closely contactable with and fixable to the tube and the tubular body, and sealably encloses a fluid in an interior of the tubular cover.

\* \* \* \* \*